US 6,922,585 B2

(12) United States Patent
Zhou et al.

(10) Patent No.: US 6,922,585 B2
(45) Date of Patent: Jul. 26, 2005

(54) METHOD AND APPARATUS FOR PREDICTING RECURRING VENTRICULAR ARRHYTHMIAS

(75) Inventors: Xiaohong Zhou, Plymouth, MN (US); Vinod Sharma, Roseville, MN (US); Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 501 days.

(21) Appl. No.: 10/117,465

(22) Filed: Apr. 5, 2002

(65) Prior Publication Data

US 2003/0191403 A1 Oct. 9, 2003

(51) Int. Cl.[7] ............................................. A61B 5/046

(52) U.S. Cl. ...................... 600/518; 600/515; 607/19

(58) Field of Search ................................ 600/515–518; 607/4, 5, 9, 14, 17, 19

(56) References Cited

U.S. PATENT DOCUMENTS

| 4,417,306 | A | * | 11/1983 | Citron et al. ............... 600/521 |
| 4,428,378 | A | | 1/1984 | Anderson et al. ..... 128/419 PG |
| 5,042,497 | A | | 8/1991 | Shapland .................... 128/696 |
| 5,117,824 | A | | 6/1992 | Keimel et al. .......... 128/419 D |
| 5,545,186 | A | | 8/1996 | Olson et al. ................... 607/14 |
| 5,978,700 | A | * | 11/1999 | Nigam ........................ 600/518 |
| 6,067,473 | A | | 5/2000 | Greeninger et al. .......... 607/32 |
| 6,128,526 | A | | 10/2000 | Stadler et al. ............... 600/517 |
| 6,171,252 | B1 | | 1/2001 | Roberts ....................... 600/485 |
| 6,221,024 | B1 | | 4/2001 | Miesel ........................ 600/486 |
| 6,272,377 | B1 | * | 8/2001 | Sweeney et al. ............ 600/515 |

OTHER PUBLICATIONS

Shusterman et al., "Autonomic nervous system activity and the spontaneous initiation of ventricular tachycardia," J Am Coll Cardiol., vol. 32, p. 1891–9 (1998).*

Shusterman et al., "Autonomic nervous system activity and the spontaneous initiation of ventricular tachycardia," J Am Coll Cardiol., vol. 32, p. 1891–9 (1998).

Schmidt et al., "Heart–rate turbulence after ventricular premature beats as a predictor of mortality after acute myocardial infarction," Lancet, vol. 353, p. 1390–96 (1999).

Bansch et al., "Clusters of ventricular tachycardias signify impaired survival in patients with idiopathic dilated cardiomyopathy and implantable cardioverter defibrillators," J. Am. Coll. Cardiol., vol. 36, p. 566–73 (2000).

Exner et al., "Electrical storm presages nonsudden death: the antiarrhythmics versus implantable defibrillators (AVID) trial," Circulation, vol. 103, pp. 2066–2071 (2001).

(Continued)

*Primary Examiner*—George R. Evanisko
(74) *Attorney, Agent, or Firm*—Michael C. Soldner; Girma Wolde-Michael

(57) ABSTRACT

An implantable medical device and method are provided for assessing autonomic tone and risk factors associated with arrhythmias and, based on this assessment, an early recurrence of ventricular tachycardia or ventricular fibrillation is predicted. Specifically, changes in R—R interval, heart rate variability, patient activity, and myocardial ischemia are measured prior to and after a detected an arrhythmia episode. A recurrence score is calculated as a weighted sum of measured parameters and compared to a prediction criterion. The prediction criterion may be a preset threshold score or an individualized episode template based on previously calculated recurrence scores associated with recurring episodes. Stored parameters and episode-related data may be downloaded for offline analyses for optimizing prediction criteria and monitoring patient status.

13 Claims, 5 Drawing Sheets

OTHER PUBLICATIONS

Groenefeld et al., "Clustered incidence of spontaneously recurrent ventricular tachyarrhythmias in patients with the implanted cardioverter defibrillator," European Heart Journal, vol. 21 (suppl), p. 199 (2000).

Zhou et al., "Changes in R–R intervals during ventricular tachycardia storms in patients with implantable cardioverter–defibrillator," J. Am. Coll. Cardiol., vol. 39(suppl. A), pp. 86A–87A (2002).

* cited by examiner

METHOD AND APPARATUS FOR PREDICTING RECURRING VENTRICULAR ARRHYTHMIAS

FIELD OF THE INVENTION

The present invention relates to a medical device and, more specifically, to a device and method for assessing cardiac autonomic tone and predicting the early recurrence of ventricular tachycardia or fibrillation and triggering an alert system for initiation of possible preventive measures.

BACKGROUND OF THE INVENTION

Ventricular tachycardia (VT) and ventricular fibrillation (VF) are serious, life-threatening forms of cardiac arrhythmias. Implantable medical devices, referred to as implantable cardioverter defibrillators or ICDs, are capable of automatically detecting arrhythmias and delivering anti-arrhythmia therapies. Delivering anti-tachycardia pacing therapies or high-energy shock therapies may terminate VT and VF. Ventricular tachycardia termination is typically referred to as "cardioversion." Ventricular fibrillation termination is typically referred to as "defibrillation."

Nearly all of detected arrhythmias appropriately treated by an ICD do not result in death. However, some patients with ICDs do experience fatal arrhythmias. Compromised hemodynamic output during a VT or VF episode can render a patient unconscious resulting in related serious injuries or death. Patients may experience recurrent VT or VF and be subjected to repeated shock therapies, which cause great discomfort. Because of the serious consequences of VT and VF, it is desirable to predict the occurrence of VT and VF so that an ICD can be prepared to immediately deliver a therapy or take preventive measures to prevent the occurrence. Prediction of an imminent VT or VF episode also enables preventive medical treatments to be delivered.

A number of parameters for predicting a discreet VT or VF episode have been proposed including, for example, left ventricular dysfunction, myocardial ischemia, frequency of ventricular ectopic beats, heart rate variability, heart rate turbulence, or other electrocardiographic changes (see Shusterman et al., J Am Coll Cardiol. 1998;32:1891–9, and Schmidt et al., Lancet. 1999;353:1390–96). Changes in the autonomic nervous system are known contributing factors to arrhythmogenesis. The heart rate is normally regulated by a balance between the sympathetic and parasympathetic (vagal) components of the autonomic nervous system. Increased sympathetic activity, referred to as sympathetic tone, increases the heart rate and decreases heart rate variability. Increased vagal tone decreases the heart rate and increases heart rate variability. Heart rate variability (HRV) is the variation in consecutive heart rate cycles, which may be measured as ventricular cycle intervals, known as "R—R intervals," or as atrial cycle intervals, known as "A—A intervals." Changes in autonomic tone, especially in conjunction with myocardial ischemia, however, can play an important role in the development of arrhythmias. Therefore, indicators of changes in autonomic tone may be useful in predicting arrhythmias. Reference is made to U.S. Pat. No. 5,042,497 issued to Shapland.

Some patients experience recurring VT or VF episodes. Based on the ICD database, majority of VT/VF episodes occur in forms of "electrical storms" or "clustering" that is defined as a rate of 3 or more VT/VF episodes within a 24-hour period (see Groenefeld et al., European Heart Journal. 2000;21(suppl):199, and Zhou et al., J. Am. Coll. Cardiol. 2002;39(suppl. A):86A–87A). Patients who experience electrical storms are at greater risk for subsequent death than patients that experience discreet episodes of VT or VF. Electrical storms are estimated to occur in approximately 10 to 30% of patients having ICDs. (See Bansch et al., J. Am. Coll. Cardiol., 2000;36:566–73, and Exner et al., Circulation., 2001 ;1 03:2066–2071.)

The inventors of the present invention have found through retrospective study of ICD patients that changes in the cardiac cycle length prior to and after a VT or VF episode during a storm are different than changes in cardiac cycle length prior to and after a single discreet VT or VF episode. VT and VF are thought to result from a combination of transient triggering events and an underlying arrhythmogenic substrate. The inventors of the present invention hypothesize that if a transient triggering event, such as a high level of sympathetic tone, transient myocardial ischemia and/or abnormal heart dysfunction, persist following an initial VT or VF episode, an early recurrence of VT or VF is highly likely. Because changes in sympathetic tone are suspected to be one such triggering event, changes in autonomic tone as indicated by changes in heart rate as well as HRV may be useful in predicting an early recurrence of VT or VF. The poor prognosis for patients experiencing electrical storms substantiates the need for a device and method for predicting the occurrence of a storm to allow optimal medical treatment.

SUMMARY OF THE INVENTION

The present invention addresses the problem of recurrent ventricular tachycardia or ventricular fibrillation. Some of the various aspects of the present invention include: predicting an early recurrence of VT or VF, triggering a treatment for preventing an electrical storm, and identifying patients at high risk for sudden cardiac death.

These aspects of the invention are preferably realized in an implantable cardiac device for providing cardioversion and defibrillation therapy with an associated method for assessing cardiac autonomic tone. Specifically, in accordance with the present invention, assessing autonomic tone allows the prediction of an early VT or VF recurrence.

A number of features of the present invention facilitate the assessment of cardiac autonomic tone. In one aspect of the invention, R—R interval template representative of a patient's normal R—R interval pattern is obtained and a median R—R interval prior to and after a tachyarrhythmia or fibrillation episode is measured. Further, in another aspect of the invention, a heart rate variability template representative of the patient's normal heart rate variability is obtained and heart rate variability prior to and after a VT or VF episode is measured. In yet another aspect, patient physical activity level which is associated with a high level of sympathetic activity is measured. Further aspects of the invention include determining changes in heart rate prior to and following an episode; measuring the duration of a VT or VF episode that is associated with continuing heart dysfunction; and measuring the VT or VF cycle length.

The implantable cardiac device is preferably equipped with a data acquisition system for collecting R-R interval data and a memory for storing data. A central processing unit for controlling device functions in the detection and treatment of cardiac arrhythmias is also used for processing cardiac data in order to determine a number of parameters related to autonomic tone. The ICD is further equipped with an activity sensor to monitor the patient's activity level. Preferably, the ICD is also capable of detecting myocardial ischemia, for example by monitoring deviations of the sensed cardiac electrogram. Based on these parameters, a recurrence score is determined for indicating the likelihood of a VT or VF episode recurring.

In operation, R—R interval data are collected and an R—R template and a heart rate variability template are stored in memory as normal control parameters. Upon detection of a VT or VF episode, the median value of a predetermined number of R—R intervals immediately prior to the onset of the episode is taken as an R—R onset interval. The median value of a predetermined number of R—R intervals immediately after the episode termination is used to determine an R—R offset interval. Heart rate variability immediately prior to and after the VT or VF episode is also stored. A value for R—R interval changes at onset is calculated from the R—R onset and R—R template values. A value for R—R interval changes after termination is calculated from the R—R onset and R—R offset values. VT or VF episode data is also collected and stored such as the detected cycle length during the episode, the time duration of the detected episode, and the type of electrical therapy delivered for treating the episode. Of note, the calculation of R—R onset and offset intervals is not limited to determination of the median values. Other methods such as an averaged R—R value over a certain time period may be also used.

The stored parameters are then used to determine a recurrence score. This score may be calculated based on a number of weighted factors related to autonomic tone or VT/VF risk factors including any of heart rate variability, R—R interval changes, daily physical activity, and myocardial ischemia. The calculated score is compared to a predetermined threshold score for predicting a recurrent VT or VF. A score exceeding the threshold score, or within a given range of the threshold score, indicates an electrical storm is likely to occur. If an early VT or VF does recur, the score may be stored as an episode template, providing a characteristic threshold for that patient. Recurrence scores calculated for the subsequent VT or VF episode may then be compared to the episode template for predicting an electrical storm. If subsequent scores fall within a given range of the episode template, an early VT or VF recurrence is likely. A similar recurrence score indicates the same or similar presage for a VT or VF recurrence as that for the previously detected VT or VF. The episode template may be updated upon each early recurrence to more accurately track the predictive factors for an individual patient. The recurrence scores and episode template data are preferably stored in a data log for later downloading and offline analysis.

If a recurring VT or VF is predicted, a preventative therapy may be triggered. Preventative therapies can include pacing therapies, drug therapies, neurostimulation or combinations thereof. A patient may be alerted to a predicted storm by an audible sound or other notification method so that the patient may alter their current activity or seek medical attention.

Accordingly, the present invention implements multiple parameters including R—R interval changes, heart rate variability, arrhythmia risk factors such as ischemia, and previous arrhythmia episode information for improving the sensitivity and specificity in predicting a recurring episode. Further, the present invention enables characterization of the events precipitating a VT or VF episode in an individual patient and using that information in the form of an episode template for predicting a future recurring episode. By predicting this serious clinical problem, patients at high risk for sudden death may be identified and treated in the most appropriate manner known.

DETAILED DESCRIPTION OF THE INVENTION

As described above, the present invention is aimed at assessing cardiac autonomic tone and using this assessment, in conjunction with other parameters like myocardial ischemia, for predicting the recurrence of a ventricular tachycardia or fibrillation episode. The methods included in the present invention may be incorporated in an implantable or external monitoring device, or an implantable or external cardiac rhythm management device. In a preferred embodiment, the methods of the present invention are incorporated in an implantable cardiac device capable of monitoring the heart rhythm for detecting arrhythmias and delivering anti-arrhythmia therapies, such as the implantable cardioverter defibrillator (ICD) 10 shown in FIG. 1.

Figure 1:
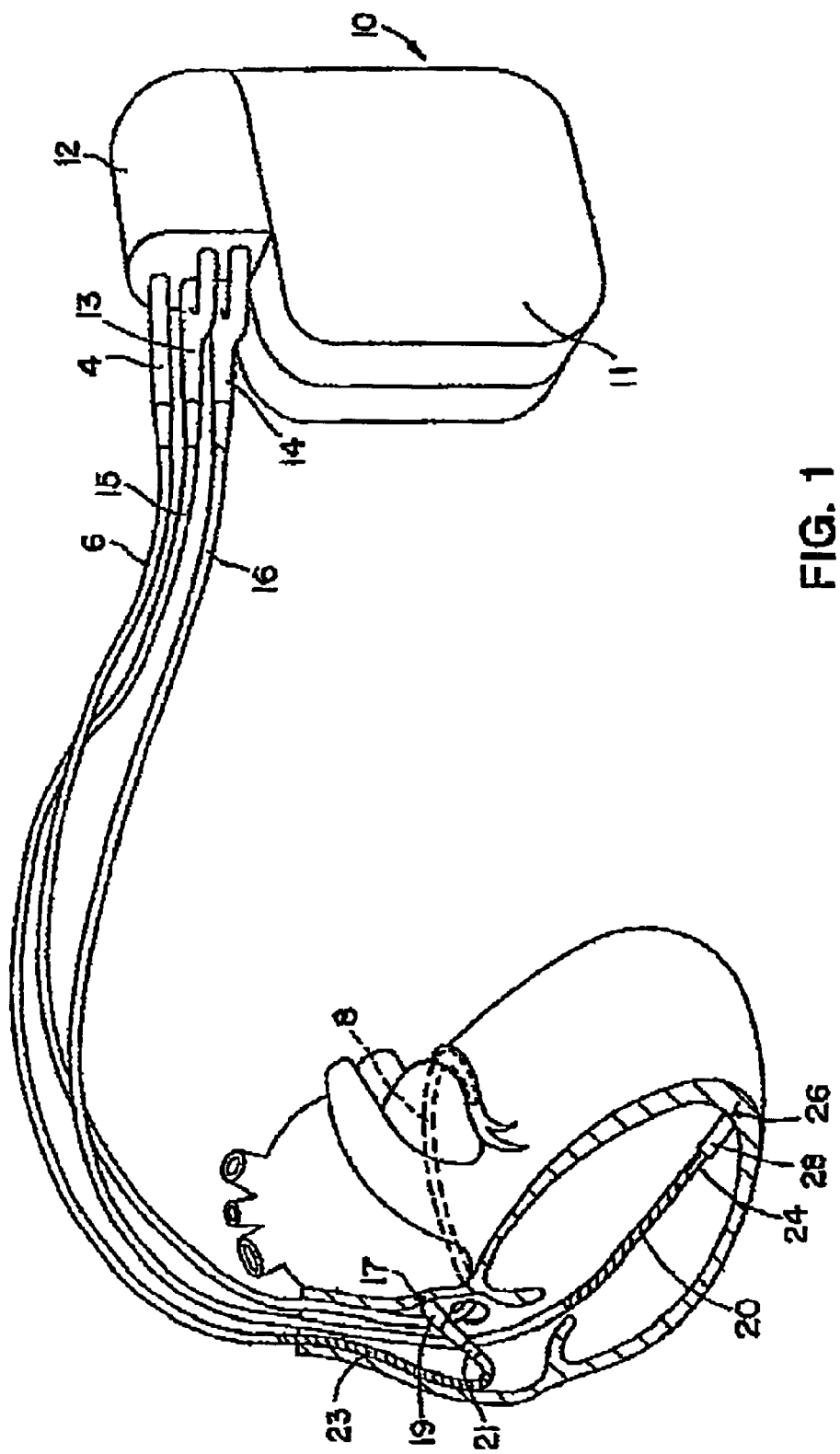
FIG. 1 is an illustration of an implantable cardiac stimulation device capable of pacemaking, cardioversion, and defibrillation and in communication with a patient's heart via three stimulation and sensing leads.

ICD 10 is shown coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the coil electrodes 8, 20 or 23 for defibrillation of the atria or ventricles. It is recognized that alternate lead systems may be substituted for the three lead system illustrated in FIG. 1.

Although three or four-chamber pacing, cardioversion and defibrillation capacity is not necessary for practicing the invention, and indeed detection of ventricular tachycardia or fibrillation can be determined by sensing only signals derived from the right ventricle, a multi-chamber system is illustrated so as to indicate the scope of the invention. It is understood that the invention may normally be practiced with a multi-chamber, dual chamber, or single chamber device.

Figure 2:
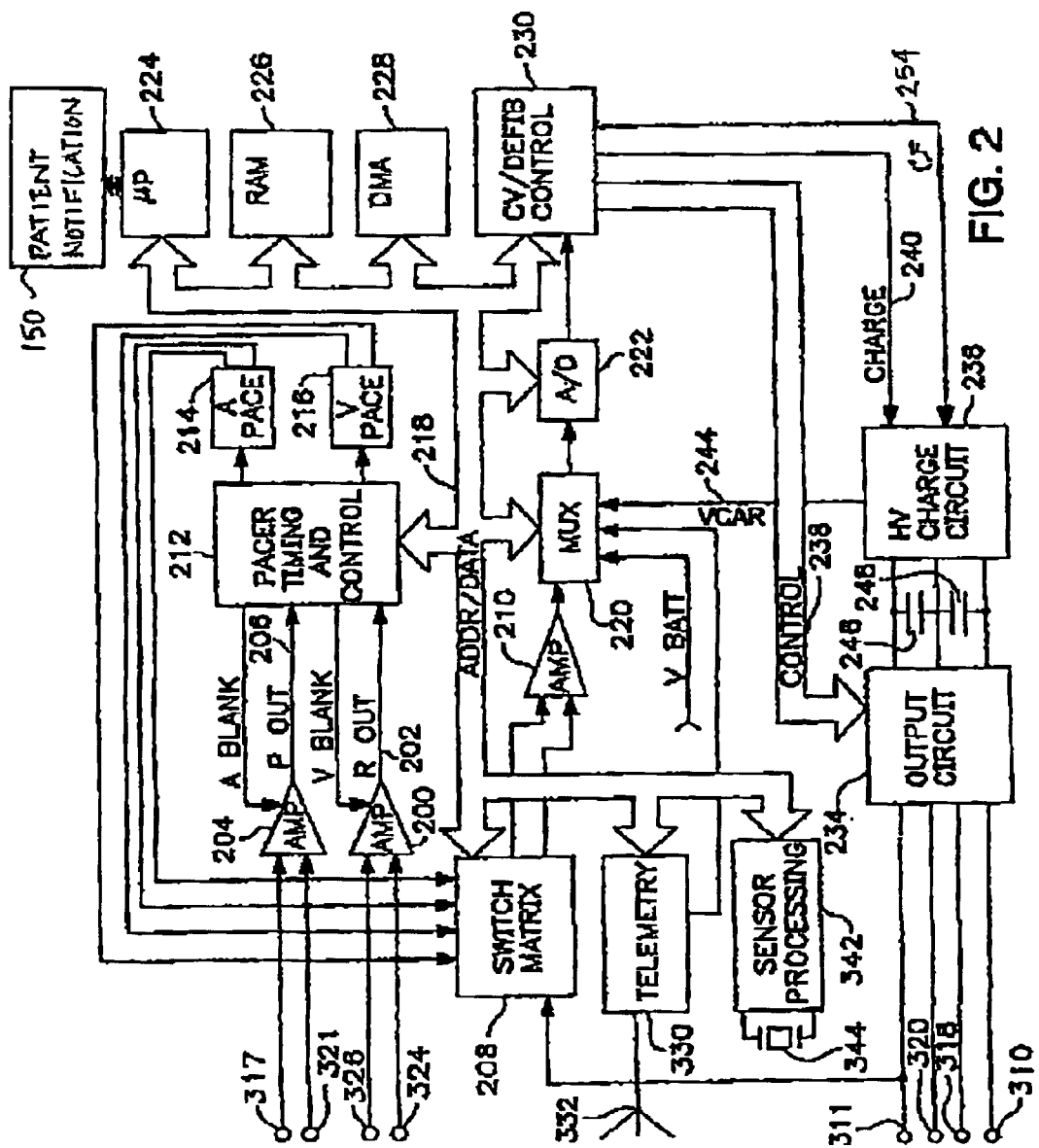
FIG. 2 is a functional, block diagram of the implantable cardiac stimulation device shown in FIG. 1.

A functional schematic diagram of the ICD 10 is shown in FIG. 2. This diagram should be taken as exemplary of the type of device in which the invention may be embodied and not as limiting. The disclosed embodiment shown in FIG. 2 is a microprocessor-controlled device, but the methods of the present invention may also be practiced in other types of devices such as those employing dedicated digital circuitry.

With regard to the electrode system illustrated in FIG. 1, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 28 respectively. Each of these connection terminals 311, 320, 310, and 318 are coupled to the high voltage output circuit 234 to facilitate the delivery of high energy shocking pulses to the heart using one or more of the coil electrodes 8, 20, and 28 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. A tachyarrhythmia recognition mechanism is described in the previously referenced U.S. Pat. No. 5,545,186 issued to Olson et al, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used. The telemetry circuit 330 is also used for communication with a patient activator in one embodiment of the present invention.

In a preferred embodiment, the device 10 is equipped with a sensor 344 and sensor processing circuitry 342. Depending on the type of sensor used, the sensor 344 may be located within the device housing 10 or external to the device housing 10 but implanted within the body of the patient. In one embodiment, the sensor 344 is used for determining the patient's activity level. The sensor 344 may take the form of a piezoelectric crystal as generally described in U.S. Pat. No. 4,428,378 issued to Anderson et al., incorporated herein by reference in its entirety.

The sensor 344 may also represent a pressure sensor for sensing a patient's blood pressure within the heart chambers or vasculature. A change in blood pressure can trigger an autonomic response, and therefore, in one embodiment of the present invention, monitoring a patient's blood pressure may be advantageous in assessing autonomic tone and predicting an electrical storm. Pressure sensors that may be implemented with the ICD 10 are generally described in U.S. Pat. No. 6,171,252 to Roberts, and U.S. Pat. No. 6,221,024 to Miesel, both patents incorporated herein by reference in their entirety.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R—R intervals and P—P intervals for detecting the occurrence of a variety of arrhythmias.

The microprocessor 224 includes associated ROM in which stored programs controlling the operation of the microprocessor 224 reside. A portion of the memory 226 may be configured as a number of re-circulating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150 used to notify the patient that a recurring VT or VF episode is predicted. Any known patient notification method may be used such as generating a perceivable twitch stimulation or an audible sound under the control of microprocessor 224. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
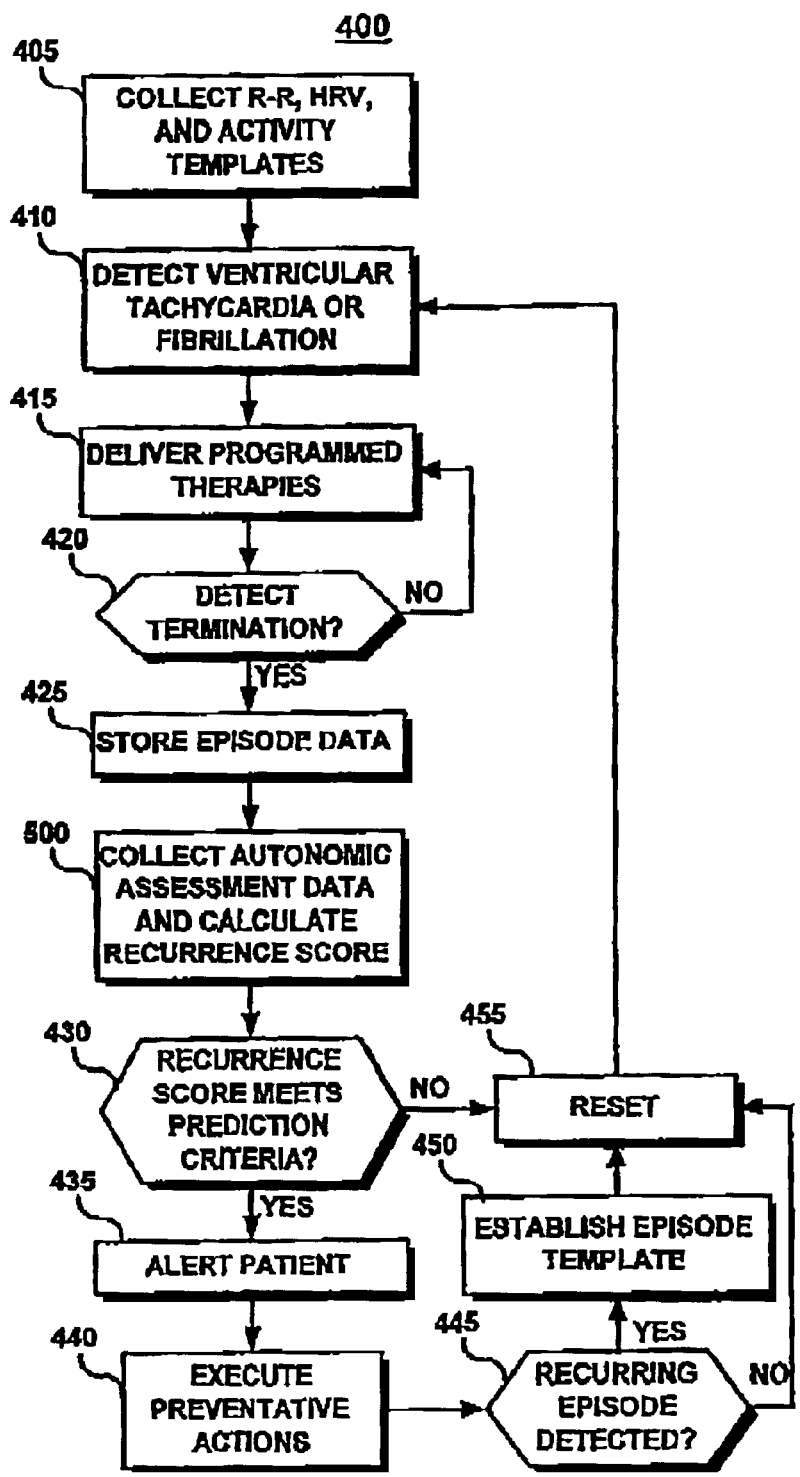
FIG. 3 is a flow chart illustrating a method performed by the device shown in FIG. 2 for predicting an early VT or VF recurrence.

In FIG. 3 a flow diagram is shown illustrating operations included in one embodiment of the present invention for assessing autonomic tone and predicting the recurrence of VT or VF. The logic steps illustrated in FIG. 3 are preferably carried out under the control of microprocessor 224. The method 400 begins at step 405 by collecting an R—R interval template, a heart rate variability (HRV) template, and a physical activity template. The R—R interval template represents the average R—R interval measured over a predetermined amount of time, for example, daily or every three to seven days. The R—R interval template may include an average daytime R—R interval and an average nighttime R—R interval. The heart rate variability (HRV) template represents an average HRV obtained from a predetermined amount of time, such as three to seven days. Likewise, an activity template represents the average activity level measured from sensor 344 over a predetermined amount of time. A correlation between the physical activity and the R—R interval is also included in the activity template, determined as the slope of the physical activity divided by the corresponding R—R interval. These templates may be obtained from data stored in a dedicated database in the memory of the ICD 10. For example, average daytime and nighttime heart rate data, daily heart rate variability and daily activity are available from stored data in the Model 7274 Marquis® Dual Chamber Implantable Cardioverter Defibrillator manufactured by Medtronic, Inc., Minneapolis, Minn. The R—R template, HRV template and activity templates may be periodically updated, for example once a week or once a month.

At step 410, the microprocessor 224 waits for a VT or VF detection. The ICD 10 delivers programmed anti-tachycardia pacing, cardioversion or defibrillation therapies according to the detected rhythm at step 415 until termination is detected at decision step 420. After termination is verified, episode-related data is stored at step 425 in a dedicated episode database within RAM 226. Episode data may include the duration of the episode, the average cycle length measured during the episode and the terminating therapy, and may correspond generally to the data stored in episode databases provided in commercially available ICDs.

At step 500, the microprocessor 224 collects data for determining indicators of autonomic tone and risk factors for VT and VF recurrence. Such data may be related to heart rate and patient activity. From this collected data, microprocessor 224 calculates a recurrence score. The operations included in the data collection and recurrence score calculation at step 500 will be further described in conjunction with FIGS. 4 and 5.

The recurrence score calculated at step 500 is compared to prediction criteria at step 430. In one embodiment, a programmable threshold level for a positive prediction may be predefined. If the recurrence score crosses the threshold, a VT or VF episode is predicted to recur. Alternatively, a range of values for a positive prediction may be predefined such that, if the recurrence score falls within that range, VT or VF is predicted to recur.

At step 435, an optional patient notification signal may be generated by notification system 150 to alert the patient to the predicted VT or VF recurrence. By notifying the patient, the patient is able to alter their current activity, seek medical attention, or self-administer a prescribed therapy.

Preventative therapies may be automatically triggered by microprocessor 224 at step 440. Preventative therapies may include pacing therapies, drug delivery, or neurostimulation. For example, overdrive pacing therapies delivered by ICD 10 may prevent the onset of a predicted storm. In alternative embodiments, the ICD 10 may be in telemetric communication with another implanted or external medical device such as a drug pump or neurostimulator. The microprocessor 224 may generate a telemetric signal to trigger the administration of a drug or the initiation of neurostimulation that may be in the form of vagal stimulation or spinal cord stimulation in an attempt to counteract the sympathetic activity that may be triggering an electrical storm. Alternatively, the method 400 may be implemented directly in a drug delivery device, a neurostimulator, or another medical device capable of delivering a preventative therapy at step 440.

At step 445, microprocessor 224 determines if a VT or VF episode did recur. A recurring episode is an episode that occurs within a predetermined amount of time of a previously detected episode, for example within 24 hours or any other specified time interval. If a recurring episode does not occur, the recurrence score and other data stored for assessing autonomic tone is reset at step 455 and the method 400 returns to step 410 to await the next VT or VF detection.

If an episode did recur, as determined at decision step 445, an episode template is established at step 450. The episode template is based on the recurrence score associated with confirmed recurrences of VT or VF. The episode template may be the score calculated for the last detected episode that was followed by an early recurrence or an average of a number of previously calculated scores. When the next VT or VF episode is detected, the prediction criteria used at step 430 for comparing to a newly calculated recurrence score may be derived from the episode template. The episode template thus provides a prediction criterion based on the patient's own triggering events and, furthermore, allows the prediction criterion to be updated over time as triggering events may change. After the episode template is established, the recurrence score and data collection is reset at step 455, and the method 400 returns to step 410 to await the next VT or VF episode detection.

Figure 4:
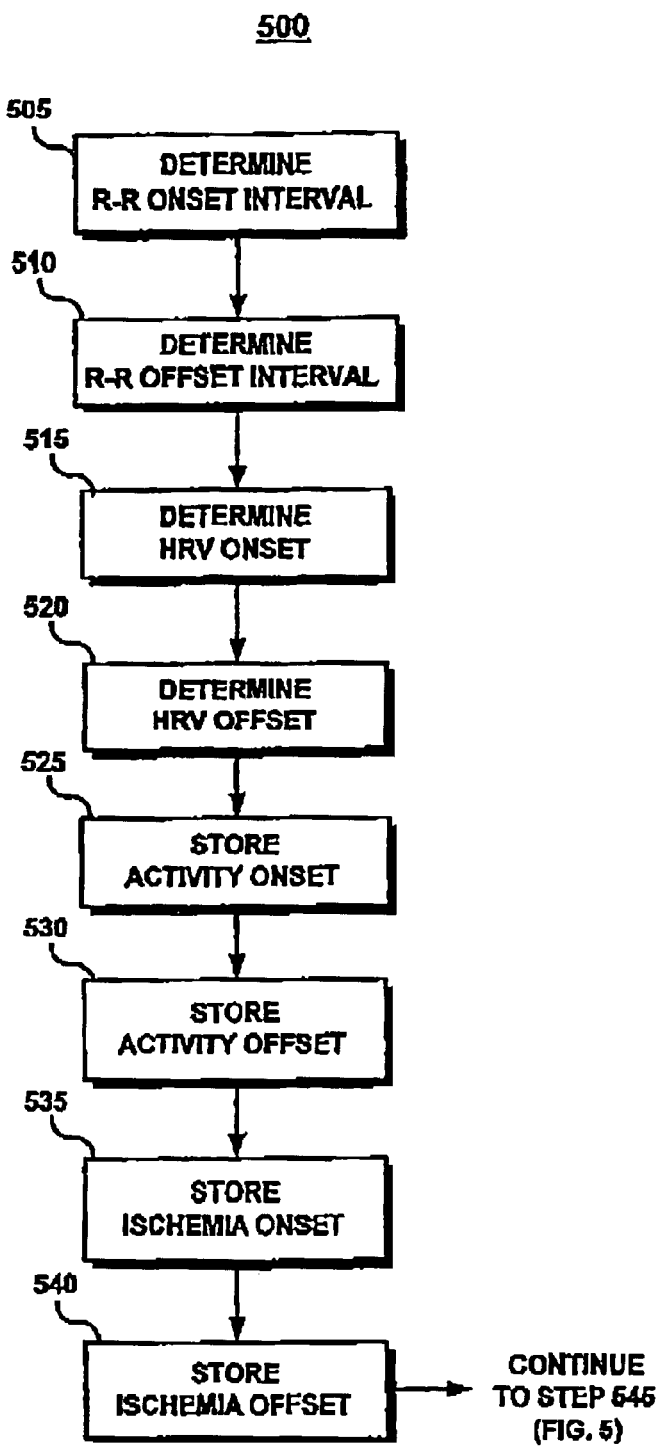
FIGS. 4 and 5 depict a flow chart illustrating the operations performed during the method of FIG. 3 for calculating a recurrence score.
Figure 5:
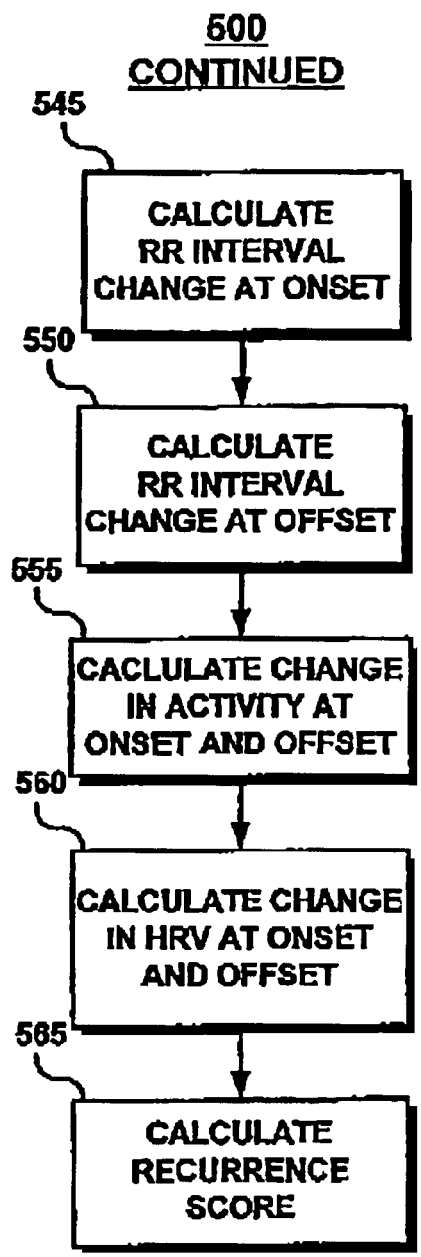

The flow chart shown in FIGS. 4 and 5 summarizes a method for collecting data related to autonomic tone and calculating a recurrence score at step 500 according to one embodiment of the present invention. At step 505, an R—R onset interval is determined based on the measured R—R intervals occurring prior to the episode detection. In one embodiment, the R—R onset interval is determined as the median cardiac cycle length at the onset of the VT or VF episode. This median value, determined from a given number of cardiac cycles, for example 10 cardiac cycles, immediately preceding the episode detection is stored in memory.

Any cardiac cycles associated with premature contractions are preferably excluded from this analysis. A premature contraction can be eliminated by determining the median interval from a number of cardiac cycles, comparing the interval from each cardiac cycle to the median, and excluding any intervals that are much longer or much shorter than the median interval. Intervals that are much shorter than the median are suspected to precede the premature contraction. Intervals that are much longer than the median are suspected to follow the premature contraction.

At step 510, an R—R offset interval is determined and stored in memory. The R—R offset interval is based on measured R—R intervals following termination of the VT or VF episode. In one embodiment, the R—R offset interval is determined as the median cardiac cycle length of a given number of R—R intervals following termination.

A measurement of heart rate variability (HRV) made prior to the detected episode is stored as HRV onset at step 515, and HRV measured following termination is stored as HRV offset at step 520. HRV indices based on differences between adjacent cardiac cycle intervals may be determined according to analyses known in the art. Automatic determination and storage of daily HRV is available in the Model 7274 Marquis® Dual Chamber Implantable Cardioverter Defibrillator, manufactured by Medtronic, Inc., Minneapolis, Minn. Onset and offset HRV values may be stored as the most recent HRV stored prior to an episode detection and the earliest HRV stored after episode termination, respectively.

At step 525, the most recent patient activity level as indicated by activity sensor 344 prior to episode detection is stored as the activity onset, and at step 530 the earliest patient activity level determined after episode termination is stored as the activity offset. If a VT or VF episode occurs during exercise with a high level of activity onset, an episode will likely recur when a high level of activity offset is continuously detected. In a preferred embodiment, ICD 10 is provided with a myocardial ischemia detection algorithm. At steps 535 and 540, the most recent myocardial ischemia determination prior to episode detection and the earliest ischemia determination after episode termination are stored as ischemia onset and the ischemia offset, respectively. The ICD 10 may detect ischemia based on changes in sensed cardiac signals. In particular, ST-segment deviations detected in the sensed myocardial electrogram signals can indicate myocardial ischemia. Like sympathetic overexcitation, myocardial ischemia has been recognized as a key factor in the genesis of VT and VF. Thus, the detection of ischemia at onset as well as offset suggests a high likelihood of a recurrence of VT or VF. Any known method for detecting myocardial ischemia may be used. One method for myocardial ischemia detection is described in U.S. Pat. No. 6,128,526 issued to Stadler et al., incorporated herein by reference in its entirety.

Steps 505 through 540 represent the data collection and storage operations included in method 500. Method 500 proceeds next to step 545 in FIG. 5 to begin calculations used in determining the recurrence score based on the stored data. At step 545, the R—R interval changes just prior to episode detection, referred to as $\Delta RR_{onset}$, is calculated. In one embodiment, $\Delta RR_{onset}$ is calculated according to the following equation:

$$\Delta RR_{onset} = (RR_{onset} - RR_{template})/RR_{template} \quad (1)$$

wherein $RR_{onset}$ is the median R—R interval prior to episode detection as determined at step 505 (FIG. 4), and $RR_{template}$ is the daily average R—R interval stored previously at step 405 of method 400 (FIG. 3).

At step 550, the R—R interval changes after termination, referred to as $\Delta RR_{offset}$, is calculated according to the following equation:

$$\Delta RR_{offset} = (RR_{offset} - RR_{onset})/RR_{onset} \quad (2)$$

wherein $RR_{offset}$ is the median R—R interval immediately following termination as determined at step 510 (FIG. 4).

At step 555, the change in patient activity level prior to episode detection ($\Delta ACT_{onset}$) and after episode termination ($\Delta ACT_{offset}$) is determined. Equation (3) represents one method for calculating $\Delta ACT_{onset}$ relative to the patient's average activity level:

$$\Delta ACT_{onset} = (ACT_{onset} - ACT_{template})/ACT_{template} \quad (3)$$

wherein $ACT_{onset}$ is the activity level last measured before episode detection as stored previously at step 525 (FIG. 4), and $ACT_{template}$ is the patient's average daily activity previously stored at step 405 of method 400 (FIG. 3). $\Delta ACT_{offset}$ may be determined relative to the activity level at onset according to equation (4):

$$\Delta ACT_{offset} = (ACT_{offset} - ACT_{onset})/ACT_{onset} \quad (4)$$

wherein $ACT_{offset}$ is the activity level measured soon after episode termination.

At step 560, changes in heart rate variability prior to episode detection ($\Delta HRV_{onset}$) and after episode termination ($\Delta HRV_{offset}$) are determined. The change in HRV at onset may be calculated relative to the patient's normal HRV according to equation (5):

$$\Delta HRV_{onset} = (HRV_{onset} - HRV_{template})/HRV_{template} \quad (5)$$

wherein $HRV_{onset}$ is the HRV prior to episode detection stored previously at step 515 (FIG. 4), and $HRV_{template}$ is the daily average HRV stored at step 405 of method 400 (FIG. 3). The change in HRV at offset may be calculated relative to the HRV at onset according to equation (6):

$$\Delta HRV_{offset} = (HRV_{offset} - HRV_{onset})/HRV_{onset} \quad (6)$$

The recurrence score is calculated at step 565 based on the stored and calculated indicators of autonomic tone obtained in steps 505 through 560. The recurrence score is preferably a weighted sum of these factors. In one embodiment, the recurrence score (SCORE) is calculated according to the following equation:

$$\begin{aligned} SCORE = &\, \alpha_1 * \Delta RR_{onset} + \alpha_2 * \Delta HRV_{onset} + \alpha_3 * \Delta ACT_{onset} + \\ &\, \alpha_4 * ISCHEMIA_{onset} + \alpha_5 * \Delta RR_{offset} + \\ &\, \alpha_6 * \Delta HRV_{offset} + \alpha_7 * \Delta ACT_{offset} + \\ &\, \alpha_8 * ISCHEMIA_{offset} \end{aligned} \quad (7)$$

wherein the calculated or measured variables are each multiplied by a unique weighting factor ($\alpha$) and then summed. A weighting factor may be zero or any real value assigned by a physician or designated by a default value stored in memory. For example, if a parameter is never found to be associated with a VT or VF occurrence in an individual patient, the associated weighting factor will be designated as zero. On the other hand, if a parameter is always found to be associated with VT or VF occurrence, a large weighting factor will be designated.

In one embodiment, a data log is stored in memory after each VT or VF episode to record the values of the measured and calculated parameters and the resulting recurrence score. This information, along with stored episode data, may be used by a physician or researcher for offline analysis to determine the optimal weighting factors for predicting recurring episodes. Such information may be updated over time to allow the recurrence score calculation to be tailored to individual patient need as their disease state changes. Stored data may also aid a physician in monitoring a patient's disease state and response to therapies.

In alternate embodiments, a change in right ventricular pressure prior to an episode detection may be included as a factor for assessing ventricular dysfunction, which is often accompanied with abnormal sympathetic tone, and included in equation (5) above for calculating a recurrence score. Changes in pressure, especially elevated end diastolic pressure as sensed by a right-ventricular pressure sensor included in sensor 344, may reflexively cause an increase in sympathetic activity, potentially triggering an arrhythmic episode. It is further recognized that other parameters considered to be indicative of autonomic tone may be included in calculating the recurrence score. The recurrence score may be calculated as a weighted sum of chosen parameters or according to alternative mathematical relations of the measured parameters. Improved specificity and sensitivity of the autonomic tone assessment included in the present invention is achieved by using multiple parameters. By accurately assessing changes in autonomic tone that are arrhythmogenic for a particular patient, patients that are at high risk for sudden cardiac death may be identified and their prognosis improved.

Thus, a method and apparatus have been described for predicting a recurring arrhythmia. While the methods included in the present invention have been described in relation to recurring VT or VF episodes, the methods described herein could readily be applied in predicting other arrhythmias, such as recurring atrial arrhythmias. Furthermore, aspects included in the present invention described in conjunction with an ICD could also be implemented in external cardioverter defibrillators, external or internal cardiac rhythm monitoring devices, or external or internal rhythm management devices, which may include drug pumps or neurostimulators. As such, the above disclosure should be considered exemplary, rather than limiting, with regard to the following claims.

What is claimed is:

1. A method for predicting a recurring arrhythmia comprising:

detecting an arrhythmia episode;

measuring a number of parameters based on said arrhythmia episode indicative of autonomic tone;

determining whether the episode is a recurring episode;

determining changes in the parameters prior to onset of the episode and subsequent to termination of the episode;

calculating a recurrence score in response to the determined changes; and predicting an arrhythmia event with high probabilistic certainty based on said recurrence score.

2. The method of claim 1 wherein said method of detecting includes measuring R—R intervals and P—P intervals.

3. The method of claim 1 wherein said method of measuring includes collecting R—R interval templates.

4. The method of claim 1 wherein said method includes collecting a heart rate variability (HRV) template.

5. The method of claim 1 wherein said method includes collecting an activity template.

6. The method according to claim 5 wherein a correlation between a physical activity and an R—R interval is included in said activity template.

7. The method of claim 1 wherein said collecting method includes determining indicators of autonomic tone and risk factors for VT and VF recurrence.

8. The method of claim 1 wherein said method of predicting includes comparing said recurrence score with a threshold, a VT or VF episode.

9. The method of claim 1 wherein said method of predicting includes using a range of value benchmarks to predict VT or VF episodes if the recurrence score falls within said range of value benchmarks.

10. The method of claim 1, wherein determining changes comprises:

determining changes in RR intervals at onset of the episode and subsequent to termination of the episode;

determining changes in activity levels at onset of the episode and subsequent to termination of the episode; and determining changes in heart rate variability at onset of the episode and subsequent to termination of the episode.

11. The method of claim 10, wherein the recurrence score is a weighted sum of the determined changes.

12. A medical device for predicting a recurring arrhythmia in a patient, comprising:

a first sensor sensing cardiac signals;

a second sensor sensing activity of the patient; and a microprocessor connected to the sensors determining whether an arrhythmia episode has occurred and whether the arrhythmia episode is a recurring episode, and determining parameters based on the arrhythmia episode indicative of autonomic tone, wherein the microprocessor determines changes In the parameters prior to onset of the episode and subsequent to termination of the episode, calculates a recurrence score in response to the determined changes, and predicts an arrhythmia event in response to the recurrence score.

13. The device of claim 12, wherein the microprocessor determines changes in RR intervals at onset of the episode and subsequent to termination of the episode, determines changes in activity levels at onset of the episode and subsequent to termination of the episode, and determines changes in heart rate variability at onset of the episode and subsequent to termination of the episode.

* * * * *